(12) United States Patent
Frechet et al.

(10) Patent No.: US 6,890,522 B2
(45) Date of Patent: *May 10, 2005

(54) COSMETIC AND PERSONAL CARE COMPOSITIONS

(75) Inventors: Jean M. J. Frechet, Oakland, CA (US); Damian Hajduk, San Jose, CA (US); Ezat Khoshdel, Wirral (GB); Mingjun Liu, Santa Clara, CA (US); Ralph B. Nielsen, San Jose, CA (US); Euan Stuart Reid, Wirral (GB); Keith Leslie Rutherford, Wirral (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/698,067

(22) Filed: Oct. 30, 2003

(65) Prior Publication Data

US 2004/0096411 A1 May 20, 2004

Related U.S. Application Data

(63) Continuation of application No. 09/969,900, filed on Oct. 3, 2001, now Pat. No. 6,663,855, which is a continuation-in-part of application No. 09/678,085, filed on Oct. 3, 2000, now abandoned.

(30) Foreign Application Priority Data

Oct. 3, 2000 (GB) .............................................. 0024182
Nov. 23, 2000 (GB) .............................................. 0028604
Nov. 23, 2000 (GB) .............................................. 0028605

(51) Int. Cl.[7] .............................. A61K 7/06; A61K 7/08; A61K 7/075; A61K 7/42; A61K 47/32

(52) U.S. Cl. .................. 424/70.11; 424/59; 424/60; 424/63; 424/70.28; 424/70.27; 424/401; 424/70.1; 424/47; 424/484; 424/486; 424/70.12; 424/70.21; 424/70.22; 424/70.15; 424/70.16; 424/70.17; 424/70.19; 514/772.4; 514/772.5; 514/772.6

(58) Field of Search .............................. 424/70.11, 59, 424/60, 70.19, 63, 70.28, 70.27, 401, 70.1, 47, 484, 486, 70.12, 70.21, 70.22, 70.15, 70.17; 514/772.4, 772.5

(56) References Cited

U.S. PATENT DOCUMENTS 4,988,506 A 1/1991 Mitra et al.
5,019,377 A 5/1991 Torgerson (Continued)

FOREIGN PATENT DOCUMENTS

EP 0 004 225 2/1979
EP 0 004 429 3/1979

(Continued)

Primary Examiner—James M. Spear
Assistant Examiner—Blessing Fubara
(74) Attorney, Agent, or Firm—Karen E. Klumas

(57) ABSTRACT

Cosmetic or personal care compositions, such as for styling hair, comprise a thermoplastic elastomer which is a block copolymer comprising a core polymer having a backbone comprising at least a proportion of C—C bonds and two or more flanking polymers. Each flanking polymer is covalently bound to an end of the core polymer and the core polymer and/or at least one of the flanking polymers is a copolymer derived from two or more monomers. The compositions comprise a cosmetically acceptable diluent or carrier.

30 Claims, 3 Drawing Sheets

SEC traces of midblock and triblock polymers

U.S. PATENT DOCUMENTS

| | | | |
|---|---|---|---|
| 5,271,930 A | 12/1993 | Walele et al. | |
| 5,472,686 A | 12/1995 | Tsubaki et al. | |
| 5,498,679 A * | 3/1996 | Moffat et al. | 526/204 |
| 5,632,998 A | 5/1997 | Midha et al. | |
| 5,660,819 A | 8/1997 | Tsubaki et al. | |
| 5,700,892 A | 12/1997 | Takiguchi et al. | |
| 5,965,115 A | 10/1999 | Bolich, Jr. et al. | |
| 5,972,356 A | 10/1999 | Peffly et al. | |
| 5,980,878 A | 11/1999 | Torgerson et al. | |
| 5,986,015 A | 11/1999 | Midha et al. | |
| 6,663,855 B2 * | 12/2003 | Frechet et al. | 424/70.11 |

FOREIGN PATENT DOCUMENTS

| | | |
|---|---|---|
| EP | 0 320 218 | 12/1988 |
| EP | 0 408 313 | 7/1990 |
| EP | 0 412 704 | 7/1990 |
| EP | 0 412 707 | 7/1990 |
| EP | 0 728 778 | 1/1996 |
| EP | 1 043 346 | 3/2000 |
| GB | 1 425 228 | 2/1976 |
| GB | 1 512 280 | 5/1978 |
| JP | 04/0191016 | 3/1992 |
| WO | 95/01383 | 1/1995 |
| WO | 95/01384 | 1/1995 |
| WO | 00/40628 | 7/2000 |
| WO | 01/96429 | 12/2001 |
| WO | 02/28358 | 4/2002 |

* cited by examiner

COSMETIC AND PERSONAL CARE COMPOSITIONS

This application is a continuation of U.S. patent application Ser. No. 09/969,900 filed on Oct. 3, 2001, now U.S. Pat. No. 6,663,855 which was a continuation-in-part of U.S. patent application Ser. No. 09/678,085 filed Oct. 3, 2000 now abandoned.

FIELD OF THE INVENTION

The present invention relates to cosmetic and personal care compositions, such as hair styling compositions, containing block copolymers, and to their use in the treatment of hair.

BACKGROUND AND PRIOR ART

Cosmetic and personal care compositions such as hair styling sprays, mousses, gels, shampoos and conditioners, frequently contain resins, gums and adhesive polymers to provide a variety of benefits, for example, film-forming ability, thickening, sensory properties and hair shaping and setting.

Polymers for use in such compositions are usually linear or graft homo- or co-polymers which contain various monomers in an alternating, random manner.

Graft copolymers are known for use as film-forming polymers in hair care and other personal care compositions. These graft copolymers typically comprise a polymeric backbone and one or more macromonomers grafted to the backbone, in which the physical and chemical attributes such as glass transition temperature and water solubility can be selected independently for the polymeric backbone and macromonomer grafts in order to provide the desired overall polymer properties.

For example, WO95/01383 and WO95/01384 describe the use of water or alcohol soluble or dispersible graft copolymers in hair and skin care compositions, in which the copolymer has a backbone and two or more polymeric side chains, and is formed by copolymerisation of randomly repeating monomer units A and B. Monomer A is selected to have a hydrophobic character and macromonomer B comprises a long hydrophilic part. EP-A-0412704, EP-A0408313 and EP-A-0412707 have suggested the use of silicone grafted acrylate copolymers in hair care applications. U.S. Pat. No. 4,988,506 describes the use of non-pressure sensitive polysiloxane-grafted copolymers in hair care compositions. U.S. Pat. No. 5,986,015 describes graft copolymers and hair care compositions containing them.

Block copolymers have an advantage over graft copolymers in that the polymer architecture can be controlled more readily. This is particularly important when designing polymers with segments of distinct physical and chemical properties for particular applications. Graft copolymers typically have many side chains and are not characterised as block copolymers.

WO 98/53794 discusses $(AB)_n$ block copolymers, where A is a silicone block and B is a vinylic block. U.S. Pat. No. 5,271,930 (Fintex Inc) describes benzoate esters of polyalkoxylated block copolymers, such as PLURONICS™, for skin and hair care compositions. U.S. Pat. No. 5,472,686 and U.S. Pat. No. 5,660,819 (both Nippon Unicar) describe non-hydrolysing block copolymers comprising a linear polysiloxane-polyoxyalkylene block as a repeating unit in cosmetic formulations. U.S. Pat. Nos. 5,965,115 and 5,972,356 (both Procter & Gamble) describe the use of silicone-polyoxyalkylene copolymer surfactants for improving stability of a polyorganosilicone emulsion in personal care compositions.

ABA triblock copolymers where the A blocks are hard and the B block is soft, are generally referred to as "thermoplastic elastomers". Such polymers are multiphase compositions in which the phases are intimately dispersed. A well known material of this type is, for example, poly(styrene-b-butadiene-b-styrene) commonly known as Kraton™ and available from Shell Chemicals Company. However, these materials are only soluble in common organic solvents such as toluene and they are not soluble in cosmetically acceptable solvents such as water and ethanol.

U.S. Pat. No. 5,980,878 discloses thermoplastic elastomers for use in hair and skin care compositions which have a backbone polymer and a plurality of polymeric side chains bound along the length of the backbone polymer. The polymers described, which have a backbone and a plurality of pendant polymer chains, are effectively graft copolymers.

International applications numbers PCT/EP00/04225 and PCT/EP00/04429 describe polysiloxane block copolymers which are built up from units of the formula [A] and [B], in which A is a polymeric block built up from radically polymerisable monomer and B is a polysiloxane block. The block copolymers may be used in cosmetic and personal care compositions.

GB 1425228 discloses hair spray or setting lotions containing ABA block copolymers. The polymers are water insoluble and organic solvents are required in the compositions in order to solubilise the polymers. In all of the examples given, the A blocks are poly(2-vinyl pyridine) and a typical B block is polybutadiene. Furthermore, in all cases each of the A blocks and the B blocks is derived from a single monomer ie, there is no copolymerisation within the A or B blocks.

Compositions suitable for application to the hair containing two-block or three-block copolymers are described in GB 1512280. The polymers contain an A block which is a homopolymer obtained from the polymerisation of an amino-substituted methacrylate ester, optionally quaternised. Throughout the document, the A and B blocks are taught as being obtained from a single monomer ie, the A and B blocks are homopolymers.

It is an object of the present invention to provide cosmetic and personal care compositions which exhibit advantages over the compositions of the prior art. In particular, the invention aims to provide a novel class of polymers for use in cosmetic and personal care compositions. The invention involves compositions containing polymers which can be produced relatively readily, and which have properties that can be tailored to the particular application. The hair treatment compositions of the invention which are useful for styling hair may have advantages in terms of longer lasting hold and/or improved feel.

SUMMARY OF THE INVENTION

In a first aspect, the present invention provides a cosmetic or personal care composition comprising a thermoplastic elastomer which is a block copolymer comprising a core polymer having a backbone comprising at least a proportion of C—C bonds and two or more flanking polymers, each flanking polymer being covalently bound to an end of the core polymer, wherein the core polymer and/or at least one of the flanking polymers is a copolymer derived from two or more monomers, and a cosmetically acceptable diluent or carrier.

Further provided by the invention in a second aspect is a cosmetic method of treating hair which comprises applying to the hair a composition of the invention.

In a third aspect, the invention provides the use of a composition of the invention for the cosmetic treatment of hair.

BRIEF DESCRIPTION OF THE DRAWINGS

The accompanying drawings illustrate, by way of example only, preferred embodiments of the invention.

DETAILED DESCRIPTION OF THE INVENTION

Figure 1:
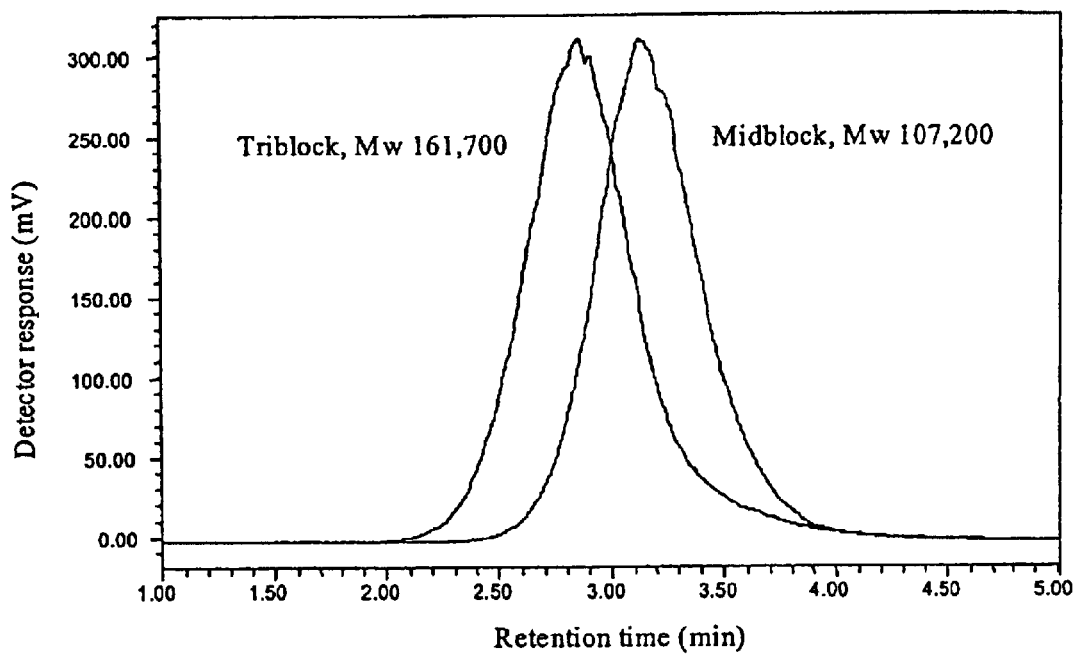
FIG. 1 is a plot showing SEC traces of an ABA copolymer after polymerization of the midblock, and after addition of the endblocks to the midblock.

The present invention involves the development of polymers for use in compositions for cosmetic and personal care applications. The compositions comprise a thermoplastic elastomer. The thermoplastic elastomer is a block copolymer comprising a core polymer having a backbone comprising at least a proportion of C—C (ie, carbon-carbon) bonds and two or more flanking polymers. The linkages in the backbone of the core polymer preferably comprise greater than 50%, more preferably greater than 75%, most preferably greater then 95%, such as, for example, at least 99% (these percentages being by number) C—C bonds. In some cases, the backbone may contain 100% (by number) C—C bonds. Other bonds which may be present in the backbone of the core polymer, in addition to the C—C bonds, include, for example, C—O bonds. The flanking polymers are bound to an end of the core polymer. Preferably, the flanking polymers comprise at least a proportion of C—C (ie, carbon-carbon) bonds. The linkages in the backbone of the flanking polymer preferably comprise greater than 50%, more preferably greater than 75%, most preferably greater then 95%, such as, for example, at least 99% (these percentages being by number) C—C bonds. In some cases, the backbone of the flanking polymer may contain 100% (by number) C—C bonds. Other bonds which may be present in the backbone of the flanking polymer, in addition to the C—C bonds, include, for example, C—O bonds.

The core polymer can take a number of different forms. For example, the core polymer may be linear or star-shaped (the latter polymers also being termed "aerial"). Star-shaped polymers may have three or more arms. When the core polymer is linear, a flanking polymer is bound to each end of the core polymer and the resulting block copolymer is an ABA block copolymer; this is a preferred embodiment of the present invention. When the core polymer is star-shaped, a flanking polymer is bound to each end of the core polymer and the block copolymer therefore contains as many flanking polymers as there are points or free ends in the star shaped polymer. For example, if the star shaped core polymer has four ends the block copolymer will comprise four flanking polymer groups.

Therefore, the block copolymer may have the structure $(AB)_n$-Core, where A and B are polymeric blocks, n is 2 or more (preferably 2, or 4, 6, 8 or 12) and Core is a non-polymeric linking core. For ABA block copolymers, there may or may not be a non-polymeric core in the B block, depending on how polymerisation is carried out. Preferably, at least one of blocks A and B is a random block comprising two or more monomers, wherein at least one of the two or more monomers is hydrophilic and at least one of the two or more monomers is hydrophobic; additionally, the absolute difference in log p values between the hydrophobic and hydrophilic monomers is preferably at least about 0.5. More preferably, the flanking polymers are random copolymers.

Usually, the flanking polymer (such as component A in an ABA block polymer) comprises or consists of a material that is hard at room temperature (ie, it has a high Tg) but becomes soft and fluid upon heating. Such materials are known in the art as "hard" blocks. The core polymer (such as component B in an ABA block copolymer) comprises or consists of a material that is soft at room temperature (ie, it has a low Tg). Materials of this latter type are known in the art as "soft blocks".

The glass transition temperature (Tg) of the flanking polymer (eg, in the case of an ABA block copolymer, the A blocks) is typically from 0 to 300° C., preferably from 25 to 175° C., more preferably from 30 to 150° C. The glass transition temperature of the core polymer (eg, in the case of an ABA block copolymer, the B blocks) is typically from −200 to 150° C., preferably from −100 to 75° C., more preferably from −100 to 50° C., most preferably from −75 to 50° C. (such as from −75 to less than 30° C.). Those skilled in the art will appreciate that the particular Tg values in any given case will depend on the overall nature of the polymer and the identity of the particular core and flanking polymers. The main requirement is that the flanking polymers will constitute hard blocks, whilst the core polymer will be a soft block. Typically, this means that the Tg of the flanking polymers will be higher than that of the core polymer.

Tg or glass transition is a well-known term in polymer science that is used to describe the temperature at which a polymer or a segment thereof undergoes a transition from a solid or brittle material to a liquid or rubberlike material. The glass transition temperature can be measured by a variety of standard techniques that are well known in polymer science. A common technique for the determination of glass transition temperature is differential scanning calorimetry, commonly known as DSC. The glass transition phenomenon in polymers is described in polymer textbooks and encyclopaedias, for example "Principles of Polymer Chemistry", A Ravve, Plenum Press, New York and London 1995, ISBN 0-306-44873-4.

The core and flanking polymer segments are generally thermodynamically incompatible and they will therefore phase separate into multiphase compositions in which the phases are intimately dispersed.

The flanking and core polymers are typically selected in a manner so as to produce a block copolymer with balanced hydrophilic/hydrophobic character. The copolymer may be, for example, soluble in water, ethanol or mixtures thereof or soluble in other cosmetically acceptable diluents or carriers.

The copolymer is preferably soluble in a solvent selected from water, ethanol and mixtures thereof. Preferably, the polymer is soluble at a level of at least 0.1% by weight (more preferably at least 1% by weight, eg, 1 to 25% by weight) in water, ethanol or a water/ethanol mixture at 25° C. By soluble, it is meant that the polymer does not form a distinct separate phase (liquid or solid) under the conditions specified.

The core polymer typically has a number average molecular weight of from 100 to 10,000,000 Da (preferably from 2,000 to 200,000 Da, more preferably from 10,000 to 100,000 Da) and a weight average molecular weight of from 150 to 20,000,000 Da (preferably from 5,000 to 450,000 Da, more preferably from 20,000 to 400,000 Da). The flanking polymers preferably have a number average molecular weight of from 80 to 500,000 Da (preferably from 100 to 100,000 Da, more preferably from 100 to 20,000 Da) and a weight average molecular weight of from 80 to 700,000 Da (preferably from 100 to 250,000 Da, more preferably from 200 to 50,000 Da). The molar ratio of the core polymer to the flanking polymers is typically from 1:10 to 10:1. Preferably, the molar ratio of the core polymer to the flanking polymers is from 3:1 to 10:1.

The block copolymers of the invention preferably have elastic moduli of from 1 to 1000 MPa, determined at 10 Hz, 1% strain, 25° C. in a simple tension geometry after two days of equilibration at 50% relative humidity, 25° C.

The viscosity of the polymer is preferably less than 15 mPas (centipoise; cp), more preferably less than 12 mPas, such as for example in the range from 3 to 12 mpas (cp), as estimated for 5 wt % polymer in 50 vol % aqueous ethanol solution at 25° C. using capillary viscometry and assuming a viscosity for deionised water of 1 mPas. Polymers having this viscosity are particularly useful in hair styling products which are formulated as sprays. For use in other hair styling applications, the viscosity of the polymers may be well outside this range.

Preferably, the block copolymers of the invention retain a relatively high bond strength under conditions of relatively high humidity. The polymers preferably have a bond strength of at least 10 g at 40° C. and 80% relative humidity, the bond strength being determined by the method described herein in the examples in the section under the heading "Method for determining bond strengths". More preferably, the polymers have a bond strength of at least 15 g at 40° C. and 80% relative humidity, even more preferably a bond strength in the range of from 15 g to 30 g at 40° C. and 80% relative humidity. The polymers most preferably have a bond strength of at least 15 g at 25° C. and 80% relative humidity, such as, for example, a bond strength in the range of from 15 g to 80 g (such as 15 g to 70 g eg, 25 g to 70 g) at 25° C. and 80% relative humidity.

Preferably, the block copolymers of the invention have a bond strength of at least 34 g at 25° C. and 50% relative humidity and an elastic modulus of less than 0.45 GPa. More preferably, the polymer has a bond strength in the range of from 34 g to 100 g, more preferably from 34 g to 60 g at 25° C. and 50% relative humidity.

The block copolymers also preferably have an elastic modulus of less than 0.45 GPa, as determined by the method described herein in the examples in the section under the heading "Method for determining elastic modulus". Preferably, the polymer has an elastic modulus in the range of from 0.01 to 0.45 GPa, more preferably 0.05 to 0.45 GPa, most preferably 0.1 to 0.45 GPa.

The fact that the polymer retains a degree of bond strength at relatively high temperatures and high humidity means that the styling composition can continue to be effective at styling hair under these conditions.

Preferably, the polymer consists essentially of (ie, contains at least 95% and preferably substantially 100%) atoms selected from carbon, hydrogen, oxygen and nitrogen.

It will be appreciated that the particular bond strength of the polymer, which is most suitable for use in a composition of the invention, will depend on the nature of the intended market for the styling composition. The needs of the particular market will be dictated by, for example, typical temperature and humidity conditions in the geographical location defining that market (regions of higher temperature and/or humidity requiring higher bond strengths) and the preferences of local users of the composition (which will be dictated by hair type and fashion and/or cultural considerations). Thus, a variety of different polymers having a variety of different bond strengths and other physical properties are potentially useful in the compositions of the invention. In order to achieve the desired bond strength and humidity resistance and to balance this with the local requirements of users of hair styling compositions, the chemical composition of the polymers can be adjusted to optimise the balance of the desired bond strength with other physical properties, such as glass transition temperature and water solubility. For example, when the polymer is a block copolymer, the composition of the flanking polymers may be modified to include monomeric and/or polymeric groups derived from monomers or comonomers, such as, for example, N-isopropylacrylamide (NIPAM), methyl methacrylate (MMA), tert-butyl acrylamide and mixtures thereof to provide blocks such as, for example, methyl methacrylate-co-acrylic acid (MMA-co-AA). Therefore, each of the flanking polymers may be a random copolymer derived from at least one hydrophobic monomer and at least one hydrophilic monomer.

Each of the core and flanking polymers may, independently, comprise a combination of two or more monomers. Hence, the copolymers used in the invention include, for example, ABA and ABC. block copolymers.

The flanking polymers in each thermoplastic elastomer molecule are preferably substantially identical in terms of their composition and molecular weight. However, the flanking polymers may, alternatively, be different from each other in terms of their composition and/or molecular weight.

Preferably, the flanking polymer and/or the core polymer, more preferably both the core polymer and the flanking polymer, comprise backbones which are obtainable by free radical polymerisation of vinylic monomers. Suitable vinylic monomers include those based on acrylate/methacrylate, acrylamide and/or styrenic systems. However, other block copolymeric systems such as those derived by, for example, addition polymerisation mechanisms such as polycondensation can also be utilised, provided that the flanking and core polymers are derived from hard and soft segments, respectively.

The block copolymers of the present invention can be produced by standard polymerisation techniques such as anionic or living free radical polymerisation methodologies. Suitable methods for preparing the polymers will be known to those skilled in the art.

The core and flanking polymers may comprise different monomers or, where each of the core and flanking polymers is a copolymer, may have one or more monomers in common.

Free radically polymerisable monomers suitable for use in polymerisation methods to produce polymers suitable for use in the present invention are preferably ethylenically unsaturated monomers. The living free radical polymerisation route is preferred due to its versatility and commercial viability. By "polymerisable" is preferably meant monomers that can be polymerised in accordance with a living radical polymerisation.

By "ethylenically unsaturated" is meant monomers that contain at least one polymerisable carbon-carbon double bond (which can be mono-, di-, tri- or tetra-substituted). Either a single monomer or a combination of two or more monomers can be utilised. In either case, the monomers are selected to meet the physical and chemical requirements of the final block copolymer.

Suitable ethylenically unsaturated monomers useful herein include protected or non-protected acrylic acid and methacrylic acid and salts, esters, anhydrides and amides thereof.

The acrylic acid and methacrylic acid salts can be derived from any of the common non-toxic metal, ammonium, or substituted ammonium counter ions.

The acrylic acid and methacrylic acid esters can be derived from $C_{1-40}$ straight chain, $C_{3-40}$ branched chain, or $C_{3-40}$ carbocyclic alcohols, from polyhydric alcohols having from about 2 to about 8 carbon atoms and from about 2 to about 8 hydroxyl groups (non-limiting examples of which include ethylene glycol, propylene glycol, butylene glycol, hexylene glycol, glycerin, and 1,2,6-hexanetriol); from amino alcohols (non-limiting examples of which include aminoethanol, dimethylaminoethanol and diethylaminoethanol and their quaternised derivatives); or from alcohol ethers (non-limiting examples of which include methoxyethanol and ethoxyethanol).

The acrylic acid and methacrylic acid amides can be unsubstituted, N-alkyl or N-alkylamino mono-substituted, or N,N-dialkyl, or N,N-dialkylamino disubstituted, wherein the alkyl or alkylamino groups can be derived from $C_{1-40}$ (preferably $C_{3-10}$) straight chain, $C_{3-40}$ branched chain, or $C_{3-40}$ carbocyclic moieties. In addition, the alkylamino groups can be quaternised.

Also useful as monomers are protected and unprotected acrylic or/and methacrylic acids, salts, esters and amides thereof, wherein the substituents are on the two and/or three carbon position of the acrylic and/or methacrylic acids, and are independently selected from $C_{1-4}$ alkyl, hydroxyl, halide (—Cl, —Br, —F, —I), —CN, and —$CO_2H$, for example methacrylic acid, ethacrylic acid, alpha-chloroacrylic acid and 3-cyano acrylic acid. The salts, esters, and amides of these substituted acrylic and methacrylic acids can be defined as described above for the acrylic/methacrylic acid salts, esters and amides.

Other useful monomers include vinyl and allyl esters of $C_{1-40}$ straight chain, $C_{3-40}$ branched chain, or $C_{3-40}$ carbocyclic carboxylic acids, vinyl and allyl halides (eg, vinyl chloride, allyl chloride), (eg, vinyl pyridine, allyl pyridine); vinylidene chloride; and hydrocarbons having at least one unsaturated carbon-carbon double bond (eg, styrene, alpha-methylstyrene, t-butylstyrene, butadiene, isoprene, cyclohexadiene, ethylene, propylene, 1-butene, 2-butene, isobutylene, p-methylstyrene); and mixtures thereof.

Preferred ethylenically unsaturated monomers have the following general formula:

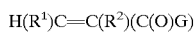

in which $R^1$ and $R^2$ are independently selected from hydrogen, $C_1$–$C_{10}$ straight or branched chain alkyl (the term alkyl, when used herein, refers to straight chain and branched groups), methoxy, ethoxy, 2-hydroxyethoxy, 2-methoxyethyl and 2-ethoxyethyl groups;

G is selected from hydroxyl, —$O(M)_{1/v}$, —$OR^3$, —$NH_2$, —$NHR^3$ and —$N(R^3)(R^4)$;

where M is a counter-ion of valency v selected from metal ions such as alkali metal ions and alkaline earth metal ions, ammonium ions and substituted ammonium ions such as mono-, di-, tri- and tetraalkylammonium ions, and each $R^3$ and $R^4$ is independently selected from hydrogen, $C_1$–$C_8$ straight or branched chain alkyl, N,N-dimethylaminoethyl, 2-hydroxyethyl, 2-methoxyethyl, and 2-ethoxyethyl.

More preferred specific monomers useful herein include those selected from protected and unprotected acrylic acid, methacrylic acid, ethacrylic acid, methyl acrylate, ethyl acrylate, α-butyl acrylate, iso-butyl acrylate, t-butyl acrylate, 2-ethylhexyl acrylate, decyl acrylate, octyl acrylate, methyl methacrylate, ethyl methacrylate, n-butyl methacrylate, iso-butyl methacrylate, t-butyl methacrylate, 2-ethylhexyl methacrylate, decyl methacrylate, methyl ethacrylate, ethyl ethacrylate, n-butyl ethacrylate, iso-butyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, 2-hydroxypropyl acrylate, hydroxypropyl methacrylate, glyceryl monoacrylate, glyceryl monoethacrylate, glycidyl methacrylate, glycidyl acrylate, acrylamide, methacrylamide, ethacrylamide, N-methyl acrylamide, N,N-dimethyl acrylamide, N,N-dimethyl methacrylamide, N-ethyl acrylamide, N-isopropyl acrylamide, N-butyl acrylamide, N-t-butyl acrylamide, N,N-di-n-butyl acrylamide, N,N-diethylacrylamide, N-octyl acrylamide, N-octadecyl acrylamide, N,N-diethylacrylamide, N-phenyl acrylamide, N-methyl methacrylamide, N-ethyl methacrylamide, N-dodecyl methacrylamide, N,N-dimethylaminoethyl acrylamide, quaternised N,N-dimethylaminoethyl acrylamide, N,N-dimethylaminoethyl methacrylamide, quaternised N,N-dimethylaminoethyl methacrylamide, N,N-dimethylaminoethyl acrylate, N,N-dimethylaminoethyl methacrylate, quaternised N,N-dimethyl-aminoethyl acrylate, quaternised N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, maleic anhydride and its half esters, fumaric acid, itaconic acid, itaconic anhydride and its half esters, crotonic acid, angelic acid, diallyldimethyl ammonium chloride, vinyl pyrrolidone vinyl imidazole, methyl vinyl ether, methyl vinyl ketone, maleimide, vinyl pyridine, vinyl pyridine-N-oxide, vinyl furan, styrene sulphonic acid and its salts, allyl alcohol, allyl citrate, allyl tartrate, vinyl acetate, vinyl alcohol, vinyl caprolactam, vinyl acetamide, vinyl formamide and mixtures thereof.

Even more preferred monomers are those selected from methyl acrylate, methyl methacrylate,.methyl ethacrylate, ethyl acrylate, ethyl methacrylate, ethyl ethacrylate, n-butyl acrylate,. n-butyl methacrylate, n-butyl ethacrylate, 2-ethylhexyl acrylate, 2-ethylhexyl methacrylate, 2-ethylhexyl ethacrylate, N-octyl acrylamide, 2-methoxyethyl acrylate, 2-hydroxyethyl acrylate, N,N-dimethylaminoethyl acrylate, N,N-dimethylaminoethyl methacrylate, acrylic acid, methacrylic acid, N-t-butylacrylamide, N-sec-butylacrylamide, N,N-dimethylacrylamide, N,N-dibutylacrylamide, N,N-dihydroxyethyllacrylamide 2-hydroxyethyl acrylate, 2-hydroxyethyl methacrylate, benzyl acrylate, 4-butoxycarbonylphenyl acrylate, butyl acrylate, 4-cyanobutyl acrylate, cyclohexyl acrylate, dodecyl acrylate, 2-ethylhexyl acrylate, heptyl acrylate, iso-butyl acrylate, 3-methoxybutyl acrylate, 3-methoxypropyl acrylate, methyl acrylate, N-butyl acrylamide, N,N-dibutyl acrylamide, ethyl acrylate, methoxyethyl acrylate, hydroxyethyl acrylate, diethyleneglycolethyl acrylate and mixtures thereof.

Particularly preferred for the flanking polymers are polymers or copolymers of an acrylamide eg, N,N-dialkylacrylamides, preferably N,N-dimethylacrylamide. Copolymers include, for example, random copolymers of an acrylamide with one or more other vinylic monomers eg, another acrylamide or an acrylate ester, as described hereinbefore. Representative examples of particularly preferred monomers for the flanking polymers therefore include, but are not restricted to: acrylamide, methacrylamide, N-tert-butylacrylamide, N-sec-butylacrylamide, N,N-dimethylacrylamide, N,N-dibutylacrylamide, N,N-dihydroxyethylacrylamide, acrylic and methacrylic acids and their sodium, potassium, ammonium salts, styrene, styrenesulphonic acid, N,N-dialkylaminoethyl acrylate, N,N-dialkylaminoethyl acrylamide, vinylformamide, tert-butyl acrylate, tert-butyl methacrylate, and, where the flanking polymer is a copolymer, mixtures thereof. N,N-dialkylacrylamides and N-alkylacrylamides, wherein the alkyl groups are $C_1$–$C_8$ straight or branched chain alkyl (particularly N,N-dimethylacrylamide), are the most preferred class of monomers for the flanking polymer, and are preferably used as copolymers with C1–C6 alkyl acrylate or methacrylate esters (such as methyl methacrylate) or acrylic acid when one or both of the flanking polymers is a copolymer.

It is preferred that the core polymer is a polymer or copolymer of an acrylate ester. Copolymers may, for example, be random copolymers of two or more (preferably two) different acrylate esters. Preferred acrylate esters are esters of acrylic acid and $C_1$–$C_8$ straight or branched chain alcohols. Representative examples of monomers for the core polymer include, but are not restricted to: benzyl ,acrylate, 4-butoxycarbonylphenyl acrylate, butyl acrylate, 4-cyanobutyl acrylate, cyclohexyl acrylate, dodecyl acrylate, 2-ethylhexyl acrylate, heptyl acrylate, iso-butyl acrylate, 3-methoxybutyl acrylate, 3-methoxypropyl acrylate, methyl acrylate, neopentyl acrylate, nonyl acrylate, octyl acrylate, phenethyl acrylate, propyl acrylate, N-butyl acrylamide, N,N-dibutyl acrylamide; ethyl acrylate, methoxyethyl acrylate, hydroxyethyl acrylate, diethyleneglycolethyl acrylate. More preferred are polymers or copolymers of a (C1–C3 alkoxy)C1–C6 alkyl acrylate. Particularly preferred core polymers are polymers or copolymers of (2-methoxyethyl) acrylate. The copolymers may be copolymers of (2-methoxyethyl) acrylate with $C_1$ to $C_6$ alkyl acrylate esters such as, for example, t-butyl acrylate.

In one embodiment of the invention, preferred polymers are ABA block copolymers in which the A blocks are poly(N,N-dimethylacrylamide) or poly(N,N-dimethylacrylamide-co-methyl methacrylate) and the B block is poly-((2-methoxyethyl) acrylate) or poly((2-methoxyethyl) acrylate-co-tert butyl acrylate). Even more preferred are ABA block copolymers in which the A blocks are poly(N,N-dimethylacrylamide-co-methyl methacrylate) and the B block is poly-((2-methoxyethyl) acrylate) and ABA block copolymers in which the A blocks are poly(N,N-dimethylacrylamide) and the B block is poly((2-methoxyethyl) acrylate-co-tert butyl acrylate).

The block copolymers of the invention may have further polymer chains grafted onto the core polymer and/or one or more (or all) of the flanking polymers. Suitable polymer chains for grafting onto the block copolymers include, for example, silicones, and polymers derived from monomers such as acrylate and methacrylate esters (eg, esters of acrylic or methacrylic acid with $C_1$–$C_8$ straight or branched chain alcohols), styrene (optionally substituted with one or more $C_1$–$C_{12}$ straight or branched chain alkyl groups) and mixtures thereof. Other suitable polymer chains include polyalkyleneglycols, such as polyethyleneglycol or polypropyleneglycol. The polymer chains which may be grafted onto the block copolymers may be hydrophobic or hydrophilic and hydrophobic, hydrophilic or mixtures of hydrophobic and hydrophilic chains may be grafted onto the block copolymers. Suitable hydrophobic and hydrophilic macromers for the grafts are described in WO 95/06078.

ABA Block Copolymers

The preferred polymers for use in the present invention are ABA block copolymers. As used herein, "A-B-A block copolymer" refers to a polymer comprising at least three segments having at least two differing compositions and also having any one of a number of different architectures, where the monomers are not incorporated into the polymer architecture in a solely statistical or uncontrolled manner. The transition from each A block to B block may be sharply defined or may be tapered (ie, there may be a gradual compositional change from A to B blocks). Although there may be two, three, four or more monomers in a single block-type polymer architecture, it will still be referred to herein as a block copolymer. In some embodiments, the block copolymers of this invention include one or more blocks of random copolymer (referred to herein as an "R" block) together with one or more blocks of single monomers. Thus, the polymer architecture may be A-R-A, R-B-R, R-B-A, R-R'-R, A-R-B-A or A-R-B-R-A, where R and R' are random blocks of monomers A and B or of monomers B and C or more monomers. Moreover, the random block can vary in composition or size with respect to the overall block copolymer. In some embodiments, for example, the random block will account for between 5 and 80% by weight of the mass of the block copolymer. In other embodiments, the random block R will account for more or less of the mass of the block copolymer, depending on the application. Furthermore, the random block may have a compositional gradient of one monomer to the other (e.g., A:B) that varies across the random block in an algorithmic fashion, with such algorithm being either linear having a desired slope, exponential having a desired exponent (such as a number from 0.1–5) or logarithmic. The random block may be subject to the same kinetic effects, such as composition drift, that would be present in any other radical copolymerization and its composition, and size may be affected by such kinetics, such as Markov kinetics. Any of the monomers listed elsewhere in this specification may be used in the block copolymers of this invention.

A "block" within the scope of the block copolymers of this invention typically comprises about 5 or more monomers of a single type (with the random blocks being defined by composition and/or weight percent, as described above) . In preferred embodiments, the number of monomers within a single block may be about 10 or more, about 15 or more, about 20 or more or about 50 or more. Each block may have a desired architecture and thus, each block may be linear, branched (with short or long chain branches), star (with 3 or more arms), etc. Other architectures will be apparent to those of skill in the art upon review of this specification.

In one embodiment, block copolymers are assembled by the sequential addition of different monomers or monomer mixtures to living polymerization reactions. In another embodiment, the addition of a pre-assembled functionalized block (such as a telechelic oligomer or polymer) to a free radical polymerization mixture yields a block copolymer (e.g., the polymerization mixture may be controlled or "living"). Ideally, the growth of each block occurs with high conversion. Conversions are determined by NMR via integration of polymer to monomer signals. Conversions may also be determined by size exclusion chromatography (SEC) via integration of polymer to monomer peak. For UV detection, the polymer response factor must be determined for each polymer/monomer polymerization mixture. Typical conversions can be 50% to 100% for each block, more specifically in the range of from about 60% to about 90%). Intermediate conversion can lead to block copolymers with a random copolymer block separating the two or more homopolymer blocks, depending on the relative rates of polymerization and monomer addition. At high conversion, the size of this random block is sufficiently small such that it is less likely to affect polymer properties such as phase separation, thermal behaviour and mechanical modulus. This fact can be intentionally exploited to improve polymerization times for many applications without measurably affecting the performance characteristics of the resulting polymer. This is achieved by intentionally "killing" or terminating the living nature of the polymerization when a desired level of conversion (e.g., >80%) is reached by, e.g., cooling the polymerization to room temperature or by neutralizing the control agent, for example by introducing acids, bases, oxidizing agents, reducing agents, radical sources, scavengers, etc. In the absence of a radical control agent, the polymerization continues uncontrolled (typically at much higher reaction rates) until the remaining monomer is consumed.

The existence of a block copolymer according to this invention is determined by methods known to those of skill in the art. For example, those of skill in the art may consider nuclear magnetic resonance (NMR) studies of the block copolymer. Those of skill in the art would also consider the measured increase of molecular weight upon addition of a second monomer to chain-extend a living polymerization of a first monomer. Block copolymer structure can be suggested by observation microphase separation, including long range order (determined by X-ray diffraction), microscopy and/or birefringence measurements. Other methods of determining the presence of a block copolymer include mechanical property measurements, (e.g., elasticity of soft/hard/soft block copolymers), thermal analysis and chromatography (e.g., absence of homopolymer).

Measurement of optical properties, such as absorbance (color and clarity), provides information about the phase morphology and microstructure of the polymer emulsions. Thus, for example, birefringence measurements may indicate the presence of optical anisotropy resulting from microphase separation in hard/soft block copolymers. Likewise, sharp color delineations in optical micrographs of annealed polymer films can indicate the presence of ordered, microphase-separated block copolymer structure.

Block copolymers of sufficiently high molecular weight phase separate on a microscopic scale, to form periodically arranged microdomains which typically comprise predominantly one or the other polymer. These may take the form of lamellae, cylinders, spheres, and other more complex morphologies, and the domain sizes and periods are typically in the range 10–100 nm. Such microphase separation can be detected obtained in a variety of ways, including electron microscopy, x-ray or neutron scattering or reflectivity, measurement of optical anisotropy, and rheological measurements. The absence of a periodic microstructure is not necessarily evidence against having synthesized a block copolymer, as such absence may be due to low molecular weight, broad molecular weight distribution of the individual blocks, weak intermolecular interactions, or inadequate time and slow kinetics for microphase separation. However, the presence of a periodic microstructure on the 10–100 nm scale is considered extremely compelling evidence for block copolymer formation in accord with this invention. A periodic microstructure is not, however, an essential feature of the copolymers which may be used in the compositions of this invention.

Block copolymers are well-known to form terraced films, where the film thickness is restricted to integer or half-integer multiples of the microstructure period. This occurs because preferential interactions of one or the other block with the substrate and/or free surface cause a layering of the microdomains parallel to the film surface (see for example G. Coulon, D. Ausserre, and T. P. Russell, *J. Phys.* (Paris) 51, 777 (1990); and T. P. Russell, G. Coulon, V. R. Deline, and D. C. Miller, *Macromolecules* 22, 4600–6 (1989)). When observed in a reflection microscope (on a reflecting substrate such as a silicon wafer), the terracing manifests itself as a series of discrete, well-defined colors with sharp boundaries between them. The colors are a result of interference between light reflected from the top and bottom surfaces of the film, and depend on the local film thickness ("Newton's rings"). If terracing does not occur, the colors blend continuously from one into the other.

The presence of chemically homogeneous sequences within block copolymers leads to a phase transition known as microphase separation. Energetically unfavorable interactions between chemically distinct monomers drive the blocks to separate into spatially distinct domains. Since the blocks are covalently bound together, these domains are comparable in size to the dimensions of the polymers themselves. The presence of these domains alters the physical properties of the materials, giving the resulting composite many of the chemical and physical characteristics of each block.

Polymerisation Process

Although any conventional method can be used for the synthesis of the block copolymers of the invention, living free radical polymerisation is the preferred polymerisation process. Such polymerisations are described in the literature, for example: Tailored polymers by free radical processes, E Rizzardo et al, Macromol. Symp. 1999, 143 (World Polymer Congress, 37$^{th}$ International Symposium on Macromolecules, 1998), 291–307, ISSN: 102–1360: also Atom transfer radical polymerisation and controlled radical polymerisation, Z Zhang, et al, Gaofenzi Tongabo, 1999, (3) 138–144; K Matyjazewski, Classification and comparison of various controlled/"living" radical polymerisations, Book of Abstracts, 218$^{th}$ ACS National Meeting, New Orleans, Aug. 22–26 (1999), Poly-042.

In principle, any "living" free radical polymerisation techniques such as nitroxide radical controlled, atom transfer radical polymerisation (ATRP), reversible addition fragmentation chain transfer (RAFT) and catalytic chain transfer (CCT) could be used. The preferred polymerisation routes for the block copolymers of this invention are nitroxide mediated processes. Thus, a bis-nitroxide initiator may be employed to produce well-defined ABA block copolymers. The process comprises two steps. In the first step, a core polymer of a defined length is synthesised with the bis-nitroxide initiator at the "centre" of the core polymer. This involves the living polymerisation of the monomer or monomers with a bis-nitroxide initiator. After this first stage is complete, the core polymer is optionally purified or used without purification. The second step involves the introduction of the flanking polymer monomer or monomers using the same technique of living polymerisation. The polymerisation process can be closely monitored by gel permeation chromatography (GPC), NMR and viscosity measurements. The polymerisation process is preferably stopped when high conversions are achieved.

Living free radical polymerisation techniques suitable for use in the preparation of polymers for use in the invention include, for example, those described in Hawker et al., "Development of a Universal Alkoxyamine for 'Living' Free Radical Polymerizations," *J. Am. Chem. Soc.*, 1999, 121 (16), pp. 3904–3920 for a nitroxide mediated processes and in U.S. patent application Ser. No. 09/520,583, filed Mar. 8, 2000 and corresponding international application PCT/U.S.00/06176, which process is particularly preferred, and both of these applications are incorporated herein by reference.

Suitable polymerisation reactions include, for example, the following ratios of starting materials, temperature, pressure, atmosphere and reaction time. Temperatures for polymerization are typically in the range of from about 80° C. to about 130° C., more preferably in the range of from about 95° C. to about 130° C. and even more preferably in the range of from about 120° C. to about 130° C. The atmosphere may be controlled, with an inert atmosphere being preferred, such as nitrogen or argon. The molecular weight of the polymer can be controlled via controlled free radical polymerization techniques or by controlling the ratio of monomer to initiator. Generally, the ratio of monomer to initiator is in the range of from about 200 to about 800. In a nitroxide radical controlled polymerization the ratio of control agent to initiator can be in the range of from about 1 mol % to about 10 mol % and this is preferred. The polymerization may be carried out in bulk or in a suitable solvent such as diglyme. Polymerization reaction time may be in the-range of from about 0.5 hours to about 72 hours, preferably from about 1 hour to about 24 hours and more preferably from about 2 hours to about 12 hours.

The polymers used in the present invention are preferably produced by the living free radical process.

Compositions of the Invention

Compositions of the present invention are preferably formulated into hair care compositions, especially hairspray compositions, but can also be formulated into a wide variety of product types, including mousses, gels, lotions, tonics, sprays, shampoos, conditioners, rinses, hand and body lotions, facial moisturisers, sunscreens, anti-acne preparations, topical analgesics, mascaras, and the like. Compositions of the invention comprise a cosmetically acceptable diluent or carrier. Preferably, the compositions are for use in styling human hair and, more preferably, they are packaged and labelled as such.

Compositions of the invention preferably contain the polymer in an amount of from 0.01% to 30% (more preferably from 0.1 to 10%, even more preferably from 0.1 to 5%) by weight. Compositions of the invention may, optionally, comprise a fragrance or perfume and/or one or more of the optional additional components described hereinafter.

The carriers and additional components required to formulate such products vary with product type and can be routinely chosen by one skilled in the art. The following is a description of some of these carriers and additional components.

Carriers

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular thermoplastic elastomer to be used, and whether the product formulated is meant to be left on the surface to which it is applied (e.g., hair spray, mousse, tonic, or gel) or rinsed off after use (e.g., shampoo, conditioner, rinse)

The carriers used herein can include a wide range of components conventionally used in hair care compositions. The carriers can contain a solvent to dissolve or disperse the particular thermoplastic elastomer being used, with water, the $C_1$–$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Suitable spray containers are well known in the art and include conventional, non-aerosol pump sprays i.e., "atomisers", aerosol containers or cans having propellant, as described above, and also pump aerosol containers utilising compressed air as the propellant.

Where the hair care compositions are conditioners and rinses, the carrier can include a wide variety of conditioning materials. Where the hair care compositions are shampoos, the carrier can include, for example, surfactants, suspending agents, and thickeners. Hair styling creams or gels also typically contain a structurant or thickener, typically in an amount of from 0.01% to 10% by weight.

The carrier can be in a wide variety of forms. For example, emulsion carriers, including oil-in-water, water-in-oil, water-in-oil-in-water, and oil-in-water-insilicone emulsions, are useful herein. These emulsions can cover a broad range of viscosities, e.g., from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueousbased single phase solvents (e.g., where the viscosity of the solvent has been increased to form a solid or semi-solid by the addition of appropriate gums, resins, waxes, polymers, salts, and the like).

Additional Components

A wide variety of additional components can be employed in cosmetic and personal care compositions according to the present invention. Examples include the following:

hair styling polymers for hair styling compositions such as hair sprays, gels, and mousses. Hair styling polymers are well known articles of commerce and many such polymers are available commercially which contain moieties which render the polymers cationic, anionic, amphoteric or nonionic in nature. The polymers may be synthetic or naturally derived.

The amount of the polymer may range from 0.5 to 10%, preferably 0.75 to 6% by weight based on total weight of the composition.

Examples of Anionic Hair Styling Polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:

RESYN® 28–2930 available from National Starch (vinyl acetate/crotonic acid/vinyl neodecanoate copolymer);

ULTRAHOLD® 8 available from BASF (CTFA designation Acrylates/acrylamide copolymer);

the GANTREZ®ES series available from ISP corporation (esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are crosslinked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:

copolymers of N-vinylpyrrolidone and dimethylaminoethyl methacrylate, available from ISP Corporation as Copolymer 845, Copolymer 937 and Copolymer 958;

copolymers of N-vinylpyrrolidone and dimethylaminopropylacrylamide or methacrylamide, available from ISP Corporation as Styleze® CC10;

copolymers of N-vinylpyrrolidine and dimethylaminoethyl methacrylate;

copolymers of vinylcaprolactam, N-vinylpyrrolidone and dimethylaminoethylmethacrylate;

Polyquaternium-4 (a copolymer of diallyldimonium chloride and hydroxyethylcellulose);

Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;

Polyquaternium-16 (formed from methylvinylimidazolium chloride and vinylpyrrolidone), available from BASF as Luviquat® FC 370, FC 550, PC 905 and HM-552;

Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macro-grafted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

With certain of the above-described polymers it may be necessary to neutralise some acidic groups to promote solubility/dispersibility. Examples of suitable neutralising agents include 2-amino-2- methyl-1, 3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

- sunscreening agents such as 2-ethylhexyl p-methoxycinnamate, 2-ethylhexyl N,N-dimethyl-p-aminobenzoate, p-aminobenzoic acid, 2phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.
- anti-dandruff actives such as zinc pyrithione, piroctone olamine, selenium disulphide, sulphur, coal tar, and the like.
- hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.
- surfactants for hair shampoo and conditioner compositions. For a shampoo, the level is preferably from about 10% to about 30%, preferably from 12% to about 25%, by weight based on total weight of the composition. For conditioners, the preferred level of surfactant is from about 0.2% to about 3%, by weight based on total weight of the composition. Surfactants useful in compositions of the present invention include anionic, nonionic, cationic, zwitterionic and amphoteric surfactants.
- carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/C10–C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.
- emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate,Polysorbate 60, glyceryl stearate, PEG–100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.
- vitamins and derivatives thereof (e.g., ascorbic acid, vitamin E, tocopheryl acetate, retinoic acid, retinol, retinoids, and the like).
- cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).
- preservatives, antioxidants, chelators and sequestrants; and aesthetic components such as fragrances, colourings, hair nutrients and essential oils.

The invention also involves a method of styling hair by applying thereto a styling composition as is hereinabove described.

The following non-limiting Examples further illustrate the preferred embodiments of the invention. All percentages referred to are by weight based on total weight unless otherwise indicated.

EXAMPLES

Synthesis and Characterisation

The synthesis and characterization of the polymers was carried out according to the following general procedures.

Synthesis

Synthesis of the copolymers of the invention is illustrated by reference to Example 46 below. Other copolymers of the invention can be prepared in an analogous manner, as will be evident to those skilled in the art.

1. Bis-initiator

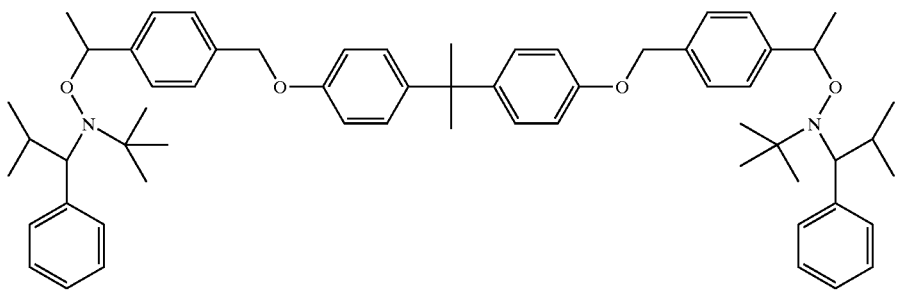

2. Free Nitroxide

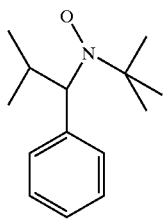

3. Monomer for Midblock (B Block)

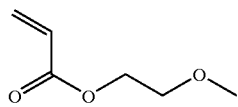

2-methoxyethyl acrylate (MEA)
4. Monomer for Endblock (A Block) Methyl Methacrylate (MMA) and:

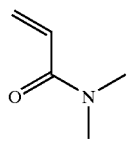

N,N-dimethylacrylamide (DMA)

5. Preparation of Midblock (B Block)

Bis-initiator (0.5557 g, 0.6147 mmol), MEA (40.00 g, 307.36 mmol) and free nitroxide (2.70 mg, 0.0123 mmol) were mixed in a 200mL flask under argon, and heated at 125° C. with vigorous stirring for 5 hrs, then cooled to room temperature. The conversion was 77% as measured by $^1$H-NMR. The reaction mixture was dissolved in acetone (60 mL), and precipitated into hexane (600 mL). The polymer was collected and dried under vacuum at 45° C., affording a clear viscous liquid (30.08 g).

6. Preparation of Triblock Copolymer (ABA)

Midblock polymer (28.88 g), diglyme (28.38 g) and free nitroxide (5.40 mg) were mixed under argon in a glove box to form a macroinitiator solution. The macroinitiator solution (2.00 g), DMA (1.198 mL) and MMA (0.821 mL) were mixed in a 15 mL flask under argon in a glove box and sealed. The solution was stirred and heated at 125° C. for 8 hrs, then cooled to room temperature. The mixture was dissolved in acetone (10 mL), and precipitated by slow addition of hexane (30 mL). The precipitation process was repeated once. The triblock copolymer was collected and dried under vacuum overnight, affording a white solid (1.88 g) (the copolymer of Example 46).

From these polymerisation methods, it will be evident to those of skill in the art that linking atoms may exist between the A and B blocks. These linking atoms are typically artefacts of the particular polymerisation mechanism employed. The presence of the linking atoms does not necessarily affect the properties of the block copolymers of the invention and polymers containing linking atoms are not intended to be excluded from the definition of the block copolymers no matter which formula is used, such as A-B-A, A-R-A, etc.

Characterization

Method For Determining Bond Strengths

For an indication of the level of hold offered by a styling polymer and to assess whether or not it adheres to hair, the bond strength between the polymer and a single fibre is measured using an automated bond strength kit. The technique is based on the principle of using an automated bond strength kit to measure the force in grams to break a bond between a polymer and two perpendicularly crossed hair fibres. This was designed by Diastron Limited (Andover, UK) and is widely used in the hair styling industry.

Apparatus

Diastron model 600 fitted with Lacquer testing carousel controlled by Series MTTWin control software (Supplied by Diastron Ltd Andover UK).

Procedure a) Preparation of Hair Fibres

Spanish hair (Supplied by Hugo Royer Sandhurst UK) having a maximum and minimum diameter of between 60 and 80 microns is first cleaned by submersion in ether for 1 minute. It is then washed with a base shampoo (16% SLES 2EO) and air dried in a straight conformation at 25deg C./50%RH for 12 hours.

b) Preparation of Styling Polymer Solution

Make up a 3% concentrated solution of the test styling polymer in a 55% water/45% ethanol mixture.

c) Diastron Control Software Parameters

The values for the test parameters within the MTTWin control panel (Lacquer Testing Routine) are set as follows:

Percentage Extension % =100
Rate mm/min=10
Max Force gmf=200
Gauge Force gmf=2
Enable Break detection=20
Carousel Set Up=25 samples, Start at 1
(Analysis Break detection=5)

d) Protocol

1. Mount the cross hair fibres on the aluminium blocks provided using an alpha cyanoacrylate adhesive (e.g. Cyanolit™).

2. Locate the mounted aluminium blocks in the slots within the lacquer testing carousel.
3. Using the Diastron crimping apparatus and mounting block, attach brass ferrule at each end of 25 hair samples at a spacing of 30 mm as determined by the mounting block.
4. Lay the crimped samples across the mounted hair fibres so that they lie perpendicularly to each other
5. Cut the crimped hair fibre using a sharp blade, above the cross-over point with the horizontal fibre, and at the end nearest to the centre of the carousel.
6. Using a 1 microliter syringe (Supplied by SGE International Pty Ltd) deposit 1 microliter of the 3% solids solution of the test styling polymer into the fibre crossover
7. Allow to dry for 3 hours under required temperature and humidity conditions ie, the conditions under which the bond strength measurement is to be carried out
8. Execute the automatic testing method using the parameters set previously
  e) Data Handling
25 separate load displacement plots are recorded for the carousel of samples. The peak load supported by the bond is recorded for each separate test and the mean load and standard deviation calculated for the carousel.

Size exclusion chromatography (SEC) characterization is performed in N,N-dimethylformamide (DMF), and molecular weights are calculated using a calibration obtained with polystyrene standards. The chain extension of triblock copolymers from midblock polymers can be clearly observed from SEC data. FIG. 1 shows data from a representative copolymer after polymerization of the midblock, and after addition of the endblocks to the midblock. Initially, the midblock polymer above has a molecular weight of 107,200 g/mol. After chain extension with DMA, the molecular weight of the resulting triblock copolymer increases to 161,700 g/mol (relative to polystyrene standards).

Triblock copolymers are also characterized by $^1$H-NMR in $CDCl_3$. Signals from different blocks can be clearly seen, and are consistent with proposed chemical structure of triblock copolymers. The composition of triblock copolymers (e.g., the molar ratio of MEA/DMA) may be calculated by comparison of relative integration of signals from different blocks.

Figure 2:
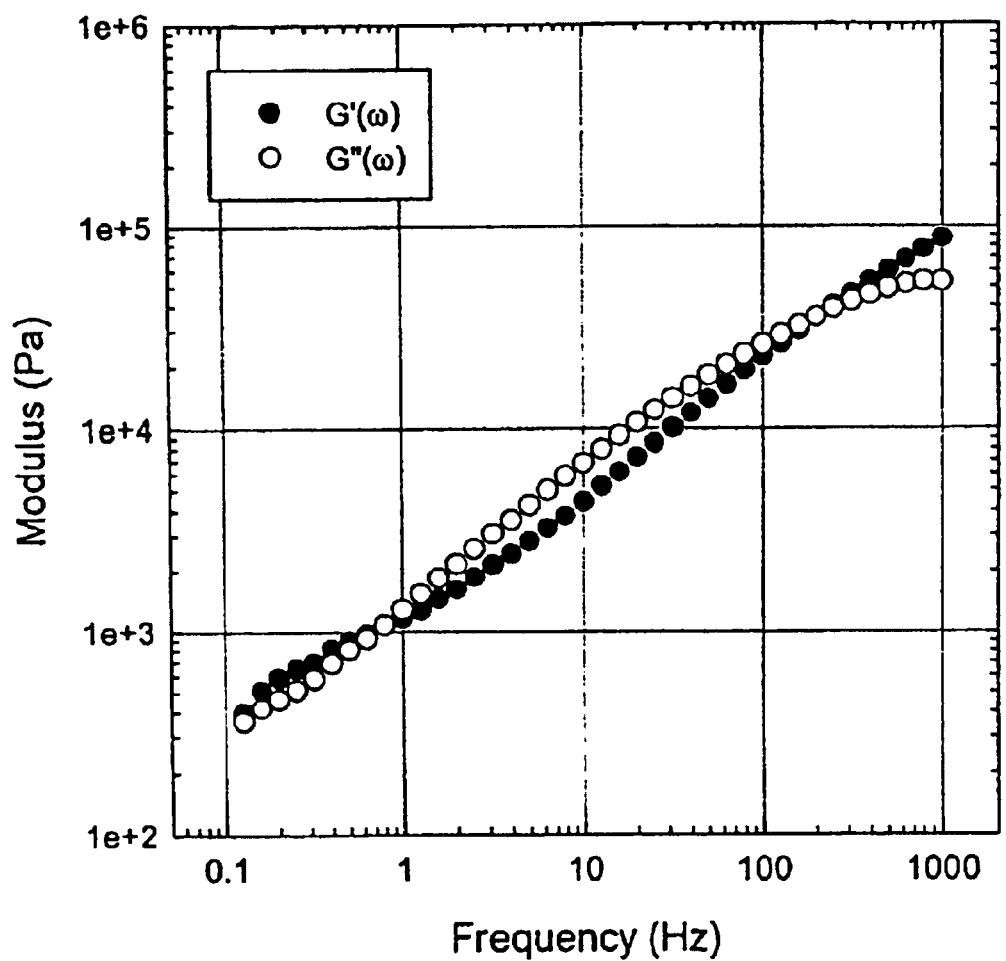
FIG. 2 shows the in-phase (G') and out-of-phase (G") components of the complex rheological modulus G* as a function of frequency ($\omega$) for a copolymer of DMA and MEA.

FIG. 2 shows by way of illustration the in-phase (G') and out-of-phase (G") components of the complex Theological modulus G* as a function of frequency ($\omega$) for a triblock copolymer of DMA and MEA (different from, but related to, polymers of the invention). A sample of a DMA-MEA-DMA copolymer with number-average block molecular weights of 12,000-52,000-12,000 g/mol and a DMA content of 38 mol% was molded at 120° C. into two disks 12 mm in diameter and 0.8 mm thick. These disks were placed in the round shear sandwich test fixture of a Rheometric Scientific DMTA-IV dynamic mechanical thermal analyzer and annealed at 120° C. for 5 minutes prior to measurement. Measurements were performed at 120° C. with a strain amplitude of 1%. At high frequencies, the response is dominated by the in-phase or elastic contribution, as expected. A crossover from in-phase to out-of-phase behavior is observed around 200 Hz. Viscoelastic models for polymer behavior generally associate crossovers with the characteristic time for molecular relaxation mechanisms; crossovers at such low frequencies are usually associated with motion of entire molecules. Below this crossover, both $G'(\omega)$ and $G''(\omega)$ scale approximately as $\omega^{-0.75}$, in contrast to the $G'(\omega) \sim \omega^{-2}$, $G''(\omega) \sim \omega^{-1}$ scaling expected for homopolymers. A second crossover is observed around 0.8 Hz which might be associated with the motion of molecular aggregates; this second crossover is generally not seen in homopolymers. The overall shape of this spectrum resembles that previously observed for other block copolymers with similar compositions (Zhao, J.; Majumdar, B.; Schulz, M. F.; Bates, F. S.; Almdal, K.; Mortensen, K.; Hajduk, D. A.; Gruner, S. M. *Macromolecules* 1996, 29, 1204–1215; Schulz, M. F.; Khandpur, A. K.; Bates, F. S.; Almdal, K.; Mortensen, K.; Hajduk, D. A.; Gruner, S. M. *Macromolecules* 1996, 29, 2857–2867).

Figure 3:
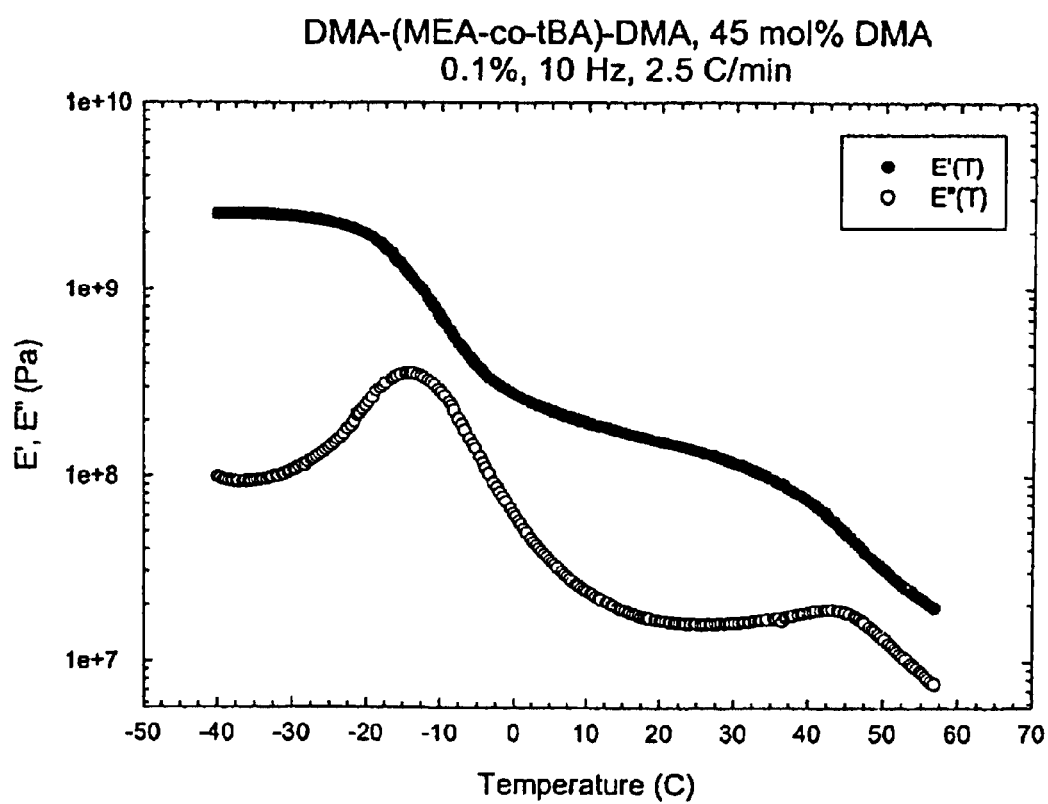
FIG. 3 shows the in-phase (E') and the out-of-phase (E") components of the complex solid modulus E* for a copolymer of DMA, MEA, and tert-butyl acrylate (tBA), which may be used in a composition of the invention, as a function of temperature at a frequency of 10 Hz, a strain amplitude of 0.1%, and a heating rate of 2.5° C./min.

FIG. 3 shows the in-phase (E') and the out-of-phase (E") components of the complex solid modulus E* for a representative triblock copolymer of DMA, MEA, and tert-butyl acrylate (tBA) as a function of temperature at a frequency of 10 Hz, a strain amplitude of 0.1%, and a heating rate of 2.5° C./min. A DMA-(MEA-co-tBA)-DMA copolymer with number-average block molecular weights of 14,000-46,000-14,000 g/mol, respectively, a DMA content of 45 mol%, and a tBA content in the midblock of 10 mol% was molded at 120° C. into a sheet 1.24 mm thick. This sheet was trimmed into a bar measuring 9.5×10 mm and mounted in the single cantilever test fixture of a Rheometric Scientific DMTA-IV dynamic mechanical thermal analyzer. The sample was cooled to −50° C. and permitted to equilibrate for at least five minutes before the settings of the sample fixture clamps were adjusted to hold the polymer in place at this temperature. The sample was then returned to −50° C. and permitted to equilibrate for another five minutes prior to measurement. The polymer exhibits two glass transitions, at −15° C. and 45° C., as indicated by maxima in the curve of E"(T). These values are considerably different than those measured for pure MEA and DMA (−50° C. and 100° C., respectively); the discrepancies reflect the finite heating rate used in this experiment, the presence of 10 mol% tBA in the MEA block (for which $T_g$=50° C.), and the mixing of MEA and DMA across the interfaces separating MEA-rich and DMA-rich domains.

Method for Determining Elastic Modulus

Modulus (E) was determined at 10 Hz, 1% strain, 25° C. in a simple tension geometry after two days of equilibration at 50% relative humidity, 25° C. Samples of polymer were molded at 120° C. into sheets 1.24 mm thick. This sheet was trimmed into a bar measuring 9.5×10 mm and mounted in the single cantilever test fixture of a Rheometric Scientific DMTA-IV dynamic mechanical thermal analyzer.

Method For Determining Viscosity

Viscosity ($\eta$) was estimated for 5 wt% polymer in 50 vol% aqueous ethanol solution at 25° C. using capillary viscometry and assuming a viscosity for deionized water of 1 cp.

Method For Determining Molecular Weights

Number average molecular weights (Mn) for midblock polymers are calculated from the monomer-to-initiator ratios, and the conversion of monomer as measured by NMR (generally about 80%), assuming the polymerization process is living. Mn for endblock polymers are calculated from DMA mole fractions and Mn values of midblock polymers. DMA mole fractions are determined by NMR.

Examples 1 to 60

The following are examples of polymers suitable for use in the present invention. Polymers containing t-butylacrylate (tBA)

All polymers are DMA-(MEA-co-tBA)-DMA copolymers; (DMA=poly(N,N-dimethylacrylamide)); (MEA-co-tBA)=poly((2-methoxyethyl) acrylate-co-tert-butyl acrylate)

| Example | Polymer Properties ABA blocks | Mw A (kDa) | Mw B (kDa) | Total Mw (kDa) | A fraction (%) | Bond Strength @25 C 5% sol. 55VOC (g) 30% | 50% | 60% (3% solids) | 80% | Flexibility E (MPa) | Viscosity (mPas) |
|---|---|---|---|---|---|---|---|---|---|---|---|
| 1 | DMA-(MEA-co-tBA) | 119 | 52 | 290 | 82 | 68.5 | 60.6 | 5.3 | | 560 | 11.6 |
| 2 | DMA-(MEA-co-tBA) | 64 | 52 | 180 | 70 | | | | | 539 | 8.8 |
| 3 | DMA-(MEA-co-tBA) | 57 | 52 | 166 | 67 | | | | | 450 | 7.9 |
| 4 | DMA-(MEA-co-tBA) | 30 | 52 | 112 | 49 | 69.5 | 53.4 | 3.9 | | 193 | 5.2 |
| 5 | DMA-(MEA-co-tBA) | 16 | 52 | 84 | 27 | | | | | <2 | 4 |
| 6 | DMA-(MEA-co-tBA) | 19 | 52 | 90 | 34 | 33.9 | 30.2 | 0 | <2 | 3.9 | |
| 7 | DMA-(MEA-co-tBA) | 23 | 52 | 98 | 40 | | | | | 15 | 4 |
| 8 | DMA-(MEA-co-tBA) | 27 | 52 | 106 | 45 | | | | | 63 | 4.6 |
| 9 | DMA-(MEA-co-tBA) | 30 | 52 | 112 | 49 | 64 | 53.3 | 3.7 | | 184 | 4.4 |
| 10 | DMA-(MEA-co-tBA) | 30 | 52 | 112 | 49 | | | | | 165 | 4.7 |
| 11 | DMA-(MEA-co-tBA) | 33 | 52 | 118 | 52 | | | | | 115 | 4.7 |
| 12 | DMA-(MEA-co-tBA) | 36 | 52 | 124 | 54 | | | | | 186 | 5 |
| 13 | DMA-(MEA-co-tBA) | 49 | 52 | 150 | 63 | | | | | 245 | 5.9 |
| 14 | DMA-(MEA-co-tBA) | 62 | 52 | 176 | 69 | 65.2 | 55.7 | 3.5 | | 478 | 6.9 |
| 15 | DMA-(MEA-co-tBA) | 4 | 28.5 | 36.5 | 27 | | | | | 2 | 5.5 |
| 16 | DMA-(MEA-co-tBA) | 7 | 28.5 | 42.5 | 39 | 37.8 | 27.1 | 0 | | 27 | 5.5 |
| 17 | DMA-(MEA-co-tBA) | 8 | 28.5 | 44.5 | 42 | | | | | 88 | 5.9 |
| 18 | DMA-(MEA-co-tBA) | 10.5 | 28.5 | 49.5 | 49 | | | | | 90 | 7.6 |
| 19 | DMA-(MEA-co-tBA) | 11 | 28.5 | 50.5 | 50 | | | | | 201 | 8.3 |
| 20 | DMA-(MEA-co-tBA) | 12 | 28.5 | 52.5 | 52 | | | | | 341 | 6.7 |
| 21 | DMA-(MEA-co-tBA) | 14 | 28.5 | 56.5 | 56 | 56.2 | 43.9 | 2 | | 236 | 8.8 |
| 22 | DMA-(MEA-co-tBA) | 16 | 28.5 | 60.5 | 60 | | | | | 554 | 7.5 |
| 23 | DMA-(MEA-co-tBA) | 21 | 28.5 | 70.5 | 66 | | | | | 608 | 6.8 |
| 24 | DMA-(MEA-co-tBA) | 25.5 | 28.5 | 79.5 | 70 | | | | | 686 | 6.8 |
| 25 | DMA-(MEA-co-tBA) | 39 | 28.5 | 106.5 | 78 | 63 | 59.6 | 2.3 | | 881 | 8.6 |
| 26 | DMA-(MEA-co-tBA) | 17.5 | 52 | 87 | 47 | 67.7 (3%) | 46 | 33.6 | | 280 | |
| 27 | DMA-(MEA-co-tBA) | 67 | 47 | 181 | 79 | 61.7 (3%) | 62.3 | 54.4 | | 740 | |
| 28 | DMA-(MEA-co-tBA) | 80 | 45 | 80 | 82 | — | — | — | — | 560 | 11.6 |
| 29 | DMA-(MEA-co-tBA) | 41 | 46 | 41 | 70 | — | — | — | — | 539 | 8.8 |
| 30 | DMA-(MEA-co-tBA) | 36 | 46 | 36 | 67 | — | — | — | — | 450 | 7.9 |
| 31 | DMA-(MEA-co-tBA) | 17 | 46 | 17 | 49 | — | — | — | — | 193 | 5.2 |
| 32 | DMA-(MEA-co-tBA) | 6 | 46 | 6 | 27 | — | — | — | — | <2 | 4.0 |
| 33 | DMA-(MEA-co-tBA) | 9 | 46 | 9 | 34 | — | — | — | — | <2 | 3.9 |
| 34 | DMA-(MEA-co-tBA) | 12 | 46 | 12 | 40 | — | — | — | — | 15 | 4.0 |
| 35 | DMA-(MEA-co-tBA) | 14 | 46 | 14 | 45 | — | — | — | — | 63 | 4.6 |
| 36 | DMA-(MEA-co-tBA) | 17 | 46 | 17 | 49 | — | — | — | — | 184 | 4.4 |
| 37 | DMA-(MEA-co-tBA) | 19 | 46 | 19 | 52 | — | — | — | — | 115 | 4.7 |
| 38 | DMA-(MEA-co-tBA) | 21 | 46 | 21 | 54 | — | — | — | — | 186 | 5.0 |
| 39 | DMA-(MEA-co-tBA) | 30 | 46 | 30 | 63 | — | — | — | — | 245 | 5.9 |
| 40 | DMA-(MEA-co-tBA) | 39 | 46 | 39 | 69 | — | — | — | — | 478 | 6.9 |

Examples 41 to 48 are (DMA-co-MMA)-MEA-(DMA-co-MMA) copolymers. Examples 49 to 56 are (DMA-co-MMA)-(MEA-co-nBA)-(DMA-co-MMA) copolymers. (DMA-co-MMA)=poly(N,N-dimethylamino acrylamide-co-methyl methacrylate); (MEA-co-nBA)=poly 2-methoxyethyl) acrylate-co-n-butyl acrylate).

| Example | Polymer Properties ABA blocks | Mw A (kDa) | Mw B (kDa) | Total Mw (kDa) | A fraction | MMA in A | MMA Frac | DMA Frac | nBA in B | nBA Frac | MEA Frac | Bond Strength @25 C 55VOC (g) 30% | 50% | 60% (3%) | 80% | 40 C 60% RH |
|---|---|---|---|---|---|---|---|---|---|---|---|---|---|---|---|---|
| 41 | (DMA-co-MMA)-MEA | 10.5 | 49 | 70 | 0.36 | 0.13 | 0.047 | 0.313 | | | 0.640 | | 19.5 | | 25.1 | 11.1 |
| 42 | (DMA-co-MMA)-MEA | 16 | 49 | 81 | 0.46 | 0.13 | 0.060 | 0.400 | | | 0.540 | | 33.2 | | 19.4 | 21.2 |
| 43 | (DMA-co-MMA)-MEA | 32 | 49 | 113 | 0.62 | 0.13 | 0.081 | 0.539 | | | 0.380 | | 41 | | 17.2 | 39.4 |
| 44 | (DMA-co-MMA)-MEA | 10.5 | 49 | 70 | 0.36 | 0.48 | 0.173 | 0.187 | | | 0.640 | | 18 | | 20.1 | 11.7 |
| 45 | (DMA-co-MMA)-MEA | 16 | 49 | 81 | 0.46 | 0.48 | 0.221 | 0.239 | | | 0.540 | | 36.2 | | 24 | 25 |
| 46 | (DMA-co-MMA)-MEA | 25 | 49 | 99 | 0.57 | 0.48 | 0.274 | 0.296 | | | 0.430 | | 42.6 | | 35.8 | 40.2 |
| 47 | (DMA-co-MMA)-MEA | 54 | 49 | 157 | 0.74 | 0.12 | 0.089 | 0.651 | | | 0.260 | | 52.6 | | 12.8 | |
| 48 | (DMA-co-MMA)-MEA | 54 | 49 | 157 | 0.74 | 0.5 | 0.370 | 0.370 | | | 0.260 | | 29.5 | | 34.5 | |

-continued

| Example | Polymer Properties ABA blocks | Mw A (kDa) | Mw B (kDa) | Total Mw (kDa) | A fraction | MMA in A | MMA Frac | DMA Frac | nBA in B | nBA Frac | MEA Frac | Bond Strength @25 C 55VOC (g) 30% | 50% | 60% (3%) | 80% | 40 C 60% RH |
|---|---|---|---|---|---|---|---|---|---|---|---|---|---|---|---|---|
| 49 | (DMA-co-MMA)-(MEA-co-nBA) | 10.7 | 48 | 69.4 | 0.37 | 0.15 | 0.056 | 0.315 | 0.30 | 0.189 | 0.441 | | 21.3 | | | |
| 50 | (DMA-co-MMA)-(MEA-co-nBA) | 17 | 48 | 82 | 0.48 | 0.14 | 0.067 | 0.413 | 0.30 | 0.156 | 0.364 | | 33.9 | | | |
| 51 | (DMA-co-MMA)-(MEA-co-nBA) | 31.5 | 48 | 111 | 0.63 | 0.15 | 0.095 | 0.536 | 0.30 | 0.111 | 0.259 | | 43.0 | | | |
| 52 | (DMA-co-MMA)-(MEA-co-nBA) | 53 | 48 | 154 | 0.74 | 0.12 | 0.089 | 0.651 | 0.30 | 0.078 | 0.182 | | 45.5 | | 14.2 | |
| 53 | (DMA-co-MMA)-(MEA-co-nBA) | 9 | 48 | 66 | 0.33 | 0.48 | 0.158 | 0.172 | 0.30 | 0.201 | 0.469 | | 17.6 | | | |
| 54 | (DMA-co-MMA)-(MEA-co-nBA) | 14 | 48 | 76 | 0.43 | 0.49 | 0.211 | 0.219 | 0.30 | 0.171 | 0.399 | | 28.0 | | | |
| 55 | (DMA-co-MMA)-(MEA-co-nBA) | 50 | 48 | 148 | 0.73 | 0.5 | 0.365 | 0.365 | 0.30 | 0.081 | 0.189 | | 36.5 | | 50.8 | |
| 56 | (DMA-co-MMA)-(MEA-co-nBA) | 23.6 | 48 | 95.2 | 0.56 | 0.5 | 0.280 | 0.280 | 0.30 | 0.132 | 0.308 | | 31.9 | | | |

Examples 57 to 60 are (MMA-co-AA)-MEA-(MMA-co-AA) Copolymers

| Example | Polymer Properties ABA blocks | Mw A | Mw B | Total Mw | A fraction | AA in A | MMA Frac | MEA Frac | AA Fraction |
|---|---|---|---|---|---|---|---|---|---|
| 57 | (MMA-co-AA)-MEA | 11 | 50 | 72 | 0.37 | 0.22 | 0.289 | 0.630 | 0.081 |
| 58 | (MMA-co-AA)-MEA | 17 | 50 | 84 | 0.49 | 0.2 | 0.392 | 0.510 | 0.098 |
| 59 | (MMA-co-AA)-MEA | 24 | 50 | 98 | 0.57 | 0.22 | 0.445 | 0.430 | 0.125 |
| 60 | (MMA-co-AA)-MEA | 49 | 50 | 148 | 0.73 | 0.22 | 0.569 | 0.270 | 0.161 |

Comparative Example

The data given above can be compared with that for a block copolymer in which the core and flanking polymers are derived from a single monomer.

A DMA-MEA-DMA block copolymer having a molecular weight of 52,000 Da for the DMA blocks and 46,000 Da for the MEA blocks-(Comparative Example) was selected for comparison with the related copolymers of Example 52. The results are as follows:

| Polymer | Bond Strength (g) at 25° C. 80% Relative Humidity |
|---|---|
| Comparative Example | 1.5 |
| Example 52 | 14.2 |

The use of copolymeric segments in the A or B blocks of an ABA block copolymer therefore gives surprising advantages in the resistance to humidity.

Examples 61 to 66

The following are examples of compositions according to the invention.

The materials used in the examples include the following:

| Material | Supplier | Function |
|---|---|---|
| Silicone emulsion X2 1787 ™ | Dow Corning | conditioning |
| VOLPO CS 50 ™ | Croda Chemicals | surfactant |
| Sepicide LD ™ | Seppic | preservative |
| Cremophor RH410 ™ | BASF | stabiliser |
| Silicone DC 200/DC 24 S ™ | Dow Corning | conditioning |
| Silwet L7602/L-720 ™ | Union Carbide | surfactant |
| CAP 40 ™ | Calor Gas | propellant |
| Carbopol 980 ™ | BF Goodrich | structurant |
| Jaguar HP-105 ™ | Rhodia | conditioning |
| Silicone Fluid 245 ™ | Dow Corning | conditioning |

Ethanol was used as SD Alcohol 40-B (92% active)

Example 61

A styling mousse is formulated as follows:

| Material | % in product (w/w) |
|---|---|
| Silicone Emulsion X2 1787 | 1.2 |
| Polymer of any of Examples 1 to 60 | 1.5 |
| VOLPO CS 50 | 0.3 |
| Sepicide LD | 0.4 |
| Cremophor RH410 | 0.2 |
| Ethanol | 7.5 |

-continued

| Material | % in product (w/w) |
|---|---|
| CAP 40 | 8.0 |
| Perfume | 0.2 |
| Water | to 100% |

Example 62

A hairspray is formulated as follows:

| Material | % in product (w/w) |
|---|---|
| Polymer of any of Examples 1 to 60 | 3.0 |
| Silicone DC 200 | 0.09 |
| Silwet L7602 | 0.09 |
| CAP 40 | 35.0 |
| Ethanol | 60.0 |
| Perfume | 0.10 |
| Water | to 100% |

Example 63

A pump spray is formulated as follows:

| Material | % w/w |
|---|---|
| Ethanol | 60.0 |
| Polymer of any of Examples 1 to 60 | 3.5 |
| Silwet L-720 | 0.3 |
| Silicone DC 24 S | 0.15 |
| Fragrance | 0.3 |
| Water | to 100% |

Example 64

A styling gel is formulated as follows:

| Material | % w/w |
|---|---|
| Polymer of any of Examples 1 to 60 | 3.8 |
| Carbopol 980 | 0.4 |
| Water | to 100% |
| Sepicide LD | 0.4 |
| Sodium hydroxide (8% 2 M) | 0.1 |
| Ethanol | 10.0 |
| Cremaphor RH410 | 0.4 |
| Jaguar HP-105 | 0.2 |
| Perfume | 0.15 |

Example 65

A 55% voc propelled aerosol composition is formulated as follows:

| Material | % w/w |
|---|---|
| Polymer of any of Examples 1 to 60 | 3.75 |

-continued

| Material | % w/w |
|---|---|
| Silicone Fluid 245 | 0.20 |
| Fragrance | 0.32 |
| Ethanol | 19.53 |
| Dimethyl ether | 35.00 |
| Sodium benzoate | 0.26 |
| Cyclohexylamine | 0.21 |
| Water | to 100% |

Example 66

A 55% voc pump hairspray composition is formulated as follows:

| Material | % w/w |
|---|---|
| Polymer of any of Examples 1 to 60 | 3.75 |
| Cyclopentasiloxane (99% active) | 0.15 |
| Benzophenone 4 | 0.0001 |
| Fragrance | 0.25 |
| Ethanol | 58.00 |
| Water | to 100% |

What is claimed is:

1. Cosmetic or personal care composition comprising a thermoplastic elastomer which is a block copolymer comprising at least one nitroxide group derived from nitroxide mediated living free radical polymerization, a core polymer block comprised of monomers selected from acrylate esters, two or more flanking polymer blocks, each flanking polymer block being covalently bound to an end of the core polymer block, wherein at least one of the core polymer or flanking polymer blocks is a random copolymer derived from two or more monomers; and a cosmetically acceptable diluent or carrier.

2. Composition as claimed in claim 1, wherein the core has a Tg of from −100° C. to 50° C.

3. Composition as claimed in claim 1, wherein the flanking polymers have a Tg of from 3° C. to 150° C.

4. Composition as claimed in claim 1, wherein the block copolymer is linear or star-shaped.

5. Composition as claimed in claim 1, wherein the block copolymer is a linear ABA block copolymer.

6. Composition as claimed in claim 5, wherein the block copolymer has the structure $(AB)_2$-Core, where A and B are polymeric blocks and Core is non-polymeric linking core.

7. Composition as claimed in claim 1, wherein the block copolymer is soluble in a solvent selected from water, ethanol and mixtures thereof.

8. Composition as claimed claim 1, wherein at least one of blocks A and B is a random block comprising two or more monomers, wherein at least one of the two or more monomers is hydrophilic and at least one of the two or more monomers is hydrophobic.

9. Composition as claimed in claim 8 wherein the absolute difference in log p values between the hydrophobic and hydrophilic monomers is preferably at least about 0.5.

10. Composition as claimed in claim 1, wherein the core polymer is a random copolymer of two or more different acrylate esters.

11. Composition as claimed in claim 1, wherein the core polymer is a polymer or copolymer of a (C1-C3 alkoxy)C1-C6 alkyl acrylate.

12. Composition as claimed claim 11, wherein the core polymer is a polymer or copolymer of (2-methoxyethyl) acrylate.

13. Composition as claimed in claim 1, wherein the flanking polymers are random copolymers of an acrylamide with one or more other vinylic monomers.

14. Composition as claimed in claim 1, wherein the flanking polymers are polymers or copolymers of N,N-dimethyl acrylamide.

15. Composition as claimed in claim 1, which comprises from 0.1 to 10% by weight of the block copolymer.

16. Composition as claimed in claim 1, wherein the core polymer has a weight average molecular weight of from 20 kDa to 500 kDa.

17. Composition as claimed in claim 1, wherein the flanking polymers have a weight average molecular weight of from 200 Da to 50 kDa.

18. Composition as claimed in claim 1, wherein the molar ratio of the core polymer to the flanking polymers is from 1:10 to 10:1.

19. Composition as claimed in claim 1, wherein the block copolymer has a bond strength of at least 10 g at 40° C. and 80% relative humidity.

20. Composition as claimed in claim 1, wherein the block copolymer has a bond strength of at least 15 g at 25° C. and 80% relative humidity.

21. Composition as claimed in claim 1, wherein the polymer has a viscosity of less than 15 cp as determined for 5 wt % polymer in 50 vol % aqueous ethanol solution at 25° C. using capillary viscometry and assuming a viscosity for deionised water of 1 mPas.

22. Composition as claimed in claim 1, wherein the block copolymer has a bond strength of at least 34 g at 25° C. and 50% relative humidity and an elastic modulus of less than 0.45 Gpa.

23. Composition as claimed in claim 1, which further comprises a fragrance or perfume.

24. Composition as claimed in claim 1, which is a hairspray, mousse or gel for styling hair.

25. Composition as claimed in claim 24, further an additional hair styling polymer.

26. Composition as claimed in claim 24, further comprising from 0.01% to 7.50% by weight of a surfactant.

27. Composition as claimed in claim 24, further comprising up to 30% by weight of a propellant.

28. Composition as claimed in claim 24 which is a hair styling cream or gel including from 0.01% to 10% by weight of a structurant or thickener.

29. A cosmetic method of treating hair which comprises the step of applying to the hair a composition comprising a thermoplastic elastomer which is a block copolymer comprising at least one nitroxide group derived from nitroxide mediated living free radical polymerization, a core polymer block comprised of monomers selected from acrylate esters, and two flanking polymer blocks, each flanking polymer block being covalently bound to an end of the core polymer block, wherein at least one of the core polymer or flanking polymer blocks is a random copolymer derived from two or more monomers; and a cosmetically acceptable diluent or carrier.

30. Method as claimed in claim 29, wherein the hair is human hair.

* * * * *